(12) United States Patent
Wollmann et al.

(10) Patent No.: US 10,466,274 B2
(45) Date of Patent: Nov. 5, 2019

(54) ARRANGEMENT FOR SPATIALLY RESOLVED DETERMINATION OF THE SPECIFIC ELECTRICAL RESISTANCE AND/OR THE SPECIFIC ELECTRICAL CONDUCTIVITY OF SAMPLES

(71) Applicant: FRAUNHOFER-GESELLSCHAFT ZUR FOERDERUNG DER ANGEWANDTEN FORSCHUNG E.V., Munich (DE)

(72) Inventors: Philipp Wollmann, Dresden (DE); Wulf Graehlert, Dresden (DE); Eric Weissenborn, Dresden (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 14 days.

(21) Appl. No.: 15/555,116

(22) PCT Filed: Mar. 2, 2016

(86) PCT No.: PCT/EP2016/054398
§ 371 (c)(1),
(2) Date: Sep. 1, 2017

(87) PCT Pub. No.: WO2016/139233
PCT Pub. Date: Sep. 9, 2016

(65) Prior Publication Data
US 2018/0045758 A1 Feb. 15, 2018

(30) Foreign Application Priority Data

Mar. 3, 2015 (DE) .......... 10 2015 203 807
Apr. 30, 2015 (DE) .......... 10 2015 208 026

(51) Int. Cl.
G01R 1/07 (2006.01)
G01R 27/26 (2006.01)
(Continued)

(52) U.S. Cl.
CPC ......... *G01R 1/071* (2013.01); *G01N 21/8422* (2013.01); *G01N 27/04* (2013.01); *G01R 27/2682* (2013.01); *G01N 2021/8438* (2013.01)

(58) Field of Classification Search
CPC .............................. G01N 27/04; G01N 1/071
See application file for complete search history.

(56) References Cited

U.S. PATENT DOCUMENTS

| 5,107,119 A | 4/1992 | Kimura et al. |
|---|---|---|
| 6,485,872 B1 | 11/2002 | Rosenthal et al. |

(Continued)

FOREIGN PATENT DOCUMENTS

| DE | 4412238 A1 * | 8/1994 | ............. G01N 21/55 |
|---|---|---|---|
| EP | 1257806 A1 | 11/2002 | |

(Continued)

*Primary Examiner* — Huy Q Phan
*Assistant Examiner* — Adam S Clarke
(74) *Attorney, Agent, or Firm* — Jacobson Holman, PLLC.

(57) ABSTRACT

An arrangement for a spatially resolved determination of the specific electrical resistance and/or of the specific electrical conductivity of a sample at different positions, in which a plurality of detectors are configured for a spatially resolved spectral analysis of electromagnetic radiation within a wavelength interval and is incident onto the detectors. A radiation onto a surface takes place with homogeneous intensity. The measurement signals of the detectors detected with spatial resolution and wavelength resolution within a wavelength interval are compared for each detected position with a wavelength-resolved function that are compared by calculation of the propagation of electromagnetic radiation in (Continued)

multilayer systems while using an optical model for a physical description of the examined sample while taking account of the wavelength-dependent progressions of the linear optical refractive indices n and of the coefficients of absorption k of all the materials and/or substances forming the sample that can be approximated by a physical function of a complex refractive index of the conductive material or substance. They are brought to a sufficient overlap with a calibration curve progression by a change of the parameters of the physical function to determine the specific electrical resistance and/or the specific electrical conductivity at different positions with spatial resolution.

9 Claims, 2 Drawing Sheets

(51) Int. Cl.
*G01N 21/84* (2006.01)
*G01N 27/04* (2006.01)

(56) References Cited

U.S. PATENT DOCUMENTS

| | | | |
|---|---|---|---|
| 8,927,933 B1 | 1/2015 | Feng | |
| 2002/0153874 A1* | 10/2002 | Jiang | G01N 21/3581 324/96 |
| 2003/0067308 A1* | 4/2003 | Bonnell | G01Q 60/54 324/662 |
| 2008/0273207 A1* | 11/2008 | Sekiguchi | G01N 21/3581 356/445 |
| 2010/0006785 A1 | 1/2010 | Finarov | |
| 2010/0179792 A1 | 7/2010 | Kurusu et al. | |
| 2013/0194577 A1* | 8/2013 | Bogdanowicz | G01N 21/1717 356/447 |
| 2014/0021967 A1 | 1/2014 | Kang et al. | |
| 2014/0259234 A1* | 9/2014 | Raschke | G01Q 10/00 850/1 |

FOREIGN PATENT DOCUMENTS

| | | | | |
|---|---|---|---|---|
| JP | 2007298480 A | 11/2007 | | |
| JP | 2011179971 A | 9/2011 | | |
| WO | WO-9326059 A1 * | 12/1993 | | G01R 1/071 |

* cited by examiner

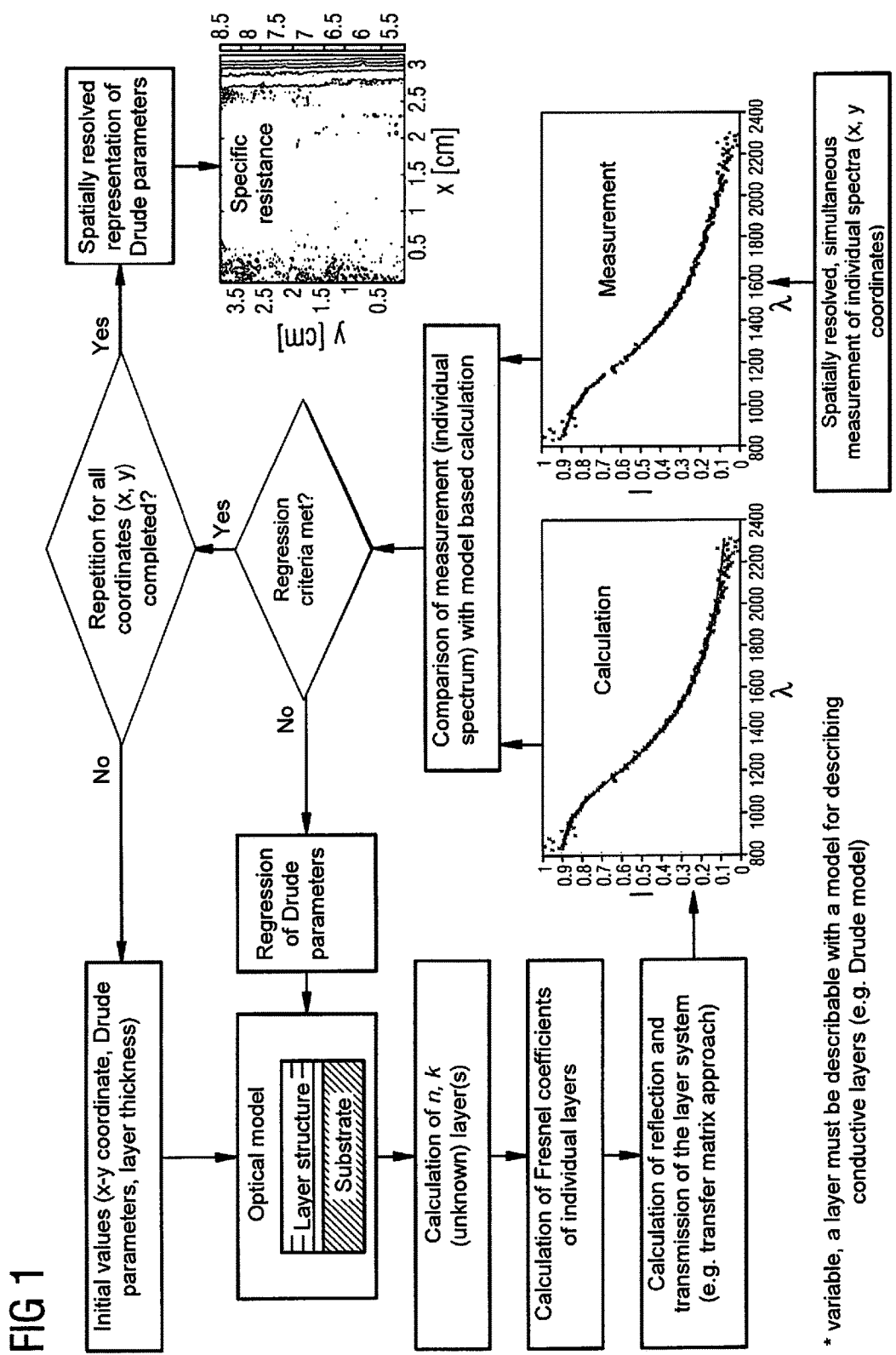

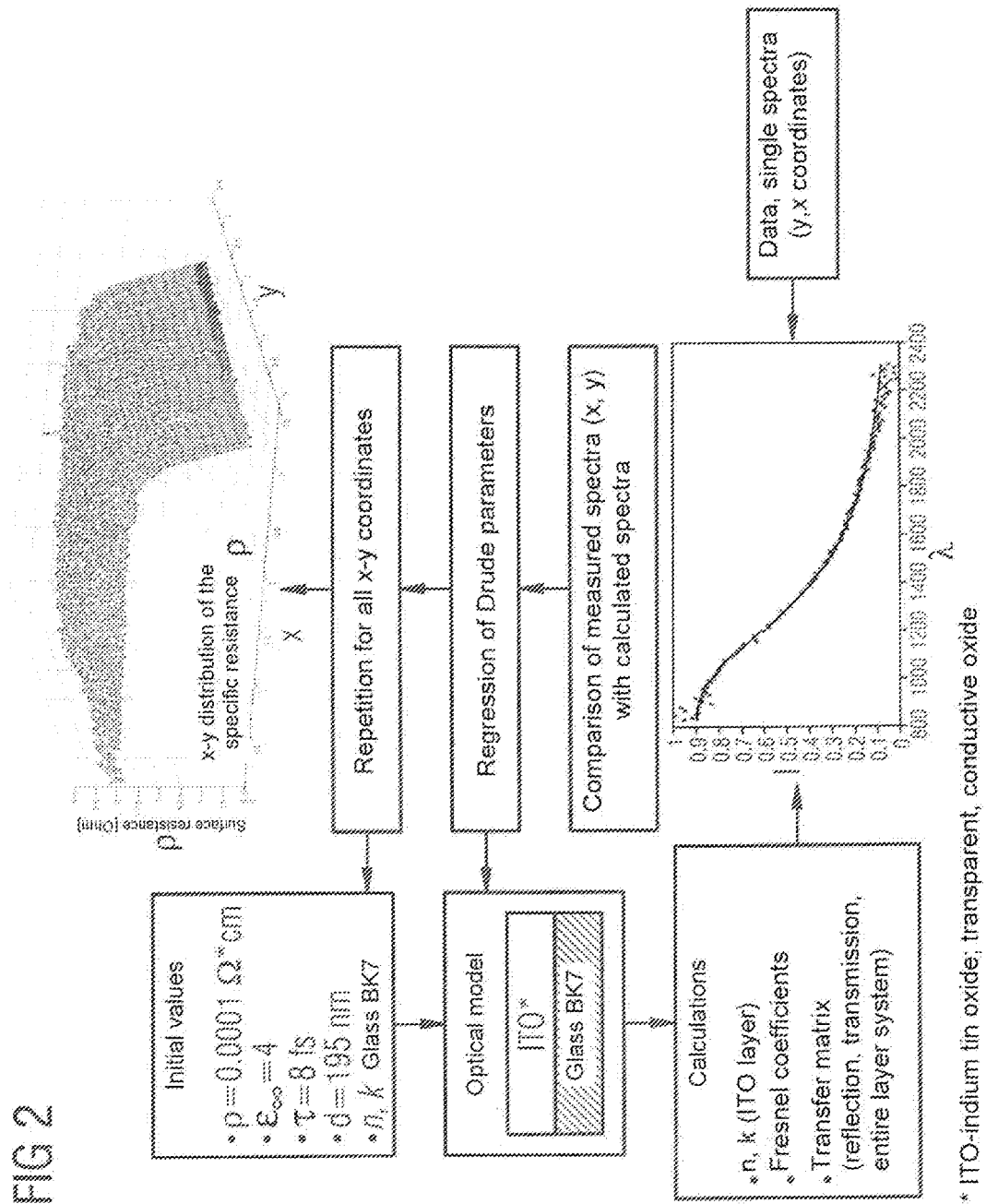

ARRANGEMENT FOR SPATIALLY RESOLVED DETERMINATION OF THE SPECIFIC ELECTRICAL RESISTANCE AND/OR THE SPECIFIC ELECTRICAL CONDUCTIVITY OF SAMPLES

The invention relates to an arrangement for a spatially resolved determination of the specific electrical resistance and/or of the specific electrical conductivity of samples, in particular of electrically conductive coatings on a surface.

The specific electrical resistance and the specific electrical conductivity have previously been determined in a spatially resolved manner by means of mapping of the so-called four-point measurement or via eddy current measurements. In this respect, however, a direct contact to a sample has to take place for the four-point measurement, which, on the one hand, represents an increased effort and/or cost and, on the other hand, effects damage to or an influencing of the surface. Corresponding accessibility for electrical connections to the measurement points is also required due to the required contact. Eddy current measurements cannot be used to check higher electrical resistances and samples of smaller electrical conductivity. In addition, it has previously been disadvantageous for the mentioned methods that with larger samples the determination has to be carried out multiple times at different positions and a limited spatial resolution nevertheless has to be accepted.

It is therefore the object of the invention to present possibilities for the contactless determination of the specific electrical resistance and/or the specific electrical conductivity simultaneously in a spatially resolved manner.

This object is achieved in accordance with the invention by an arrangement having the features of the independent claim(s). Advantageous embodiments and further developments of the invention can be realized using features designated in subordinate claims.

The invention is based on a spatially resolving optospectroscopic analysis of a sample. The spectra detected simultaneously in a spatially resolved manner are in this respect evaluated by means of a physical model or function for describing the wavelength-dependent progression of the complex refractive index (the wavelength-dependent progression of the real refractive index and of the coefficient of absorption or of the dielectric function) of electrically conductive materials/substances (e.g. Drude model) and using advantageous algorithms to describe the beam propagation of electromagnetic radiation in layer systems (e.g. Fresnel formulas) to the extent that the parameters of the physical models (e.g. Drude parameters; $\rho$-specific resistance, $\tau$-mean peak time, $\varepsilon_\infty$-high frequency dielectric constant, $\omega_P$-plasma frequency, $\mu$-charge carrier mobility) can be determined. The charge carrier density (N) in solid bodies can be directly determined using these parameters. The surface resistance can equally be determined in a spatially resolved manner while taking account of the layer thickness.

In this respect, a plurality of detectors that are configured for a spatially resolved spectral analysis of electromagnetic radiation within a wavelength interval are arranged in a row arrangement or in a row and column arrangement. The detectors are connected to an electronic evaluation unit and are arranged such that electromagnetic radiation emitted by a broadband radiation source impacts the detectors either after reflection at the surface of the sample, at a layer formed on the sample or at the surface of a layer within the sample and/or after the irradiation of a sample transparent for the electromagnetic radiation. The irradiation of the sample surface takes place in this respect such that a homogeneous intensity of the electromagnetic radiation is observed on a surface from which the electromagnetic radiation is reflected or through which it is transmitted.

The electronic evaluation unit is configured such that the measurement signals of the detectors detected with spatial resolution and with wavelength resolution within a wavelength interval are compared with a respective progression that results using the physical description of the wavelength-dependent beam propagation of electromagnetic radiation in layer systems using an optical model describing the layer system, in particular using the Drude model for a parameterized description of the wavelength-dependent progression of the complex refractive index. The measurement signals of the detectors detected with spatial resolution and wavelength resolution can be brought to a sufficient overlap with the respective model-based progressions by an advantageous selection of the Drude parameters or by their advantageous change so that the specific electrical surface resistance and/or the specific electrical conductivity of the respective sample or at least of a layer formed at the sample can be determined for the detected measurement positions and thus for their spatially resolved distribution.

The detected intensities are determined for a plurality of wavelengths using the detectors with spatial resolution at a plurality of positions.

A spectrum of detected intensity measurement values is obtained with wavelength resolution for each position observed. The curve progression of the detected intensity measurement values is compared with a curve progression that was determined once in advance for the sample system of interest (for example using ellipsometer measurements), wherein the Drude parameters used in this process represent the starting values for an iterative determination of the Drude parameters. The Drude parameters can equally be estimated.

The Drude model can be used in accordance with the following equations:

$$\varepsilon_{Drude} = \varepsilon_\infty - (\hbar^2/(\varepsilon_0 * \rho *(\tau * E^2 + (i*\hbar*E)))) \quad (1)$$

$$n = (0.5*((\varepsilon_{Drude,real}^2 + \varepsilon_{Drude,imaginary}^2)^{1/2} + \varepsilon_{Drude,real}))^{1/2} \quad (2)$$

$$k = (0.5*((\varepsilon_{Drude,real}^2 + \varepsilon_{Drude,imaginary}^2)^{1/2} - \varepsilon_{Drude,real}))^{1/2} \quad (3)$$

The real refractive indices n and the coefficients of absorption k for each energy E are calculated for the respective electrically conductive material/substance on the basis of equation (1) with reference to three parameters ($\rho$-specific resistance, $\tau$-mean peak time, $\varepsilon_\infty$-high frequency dielectric constant). Each position of the irradiated and detected surface to be observed can thus be given a corresponding curve progression in which, in accordance with equation (2), the real optical refractive indices n or, in accordance with equation (3), the coefficients of absorption k are applied in relation to the intensity measurement values detected at the respective same positions.

If too great a difference between the curve progression calculated using the three parameters and the curve progression at the detected measurement positions occurs, an adaptation can take place iteratively by changing parameters of the Drude equation (1) with which the curve progression is calculated until the two curve progressions to be compared with one another agree sufficiently.

Using an optical model, the real optical refractive index n and the coefficient of absorption k of the material of the respective sample and/or of a coating on a surface of the sample can be taken into account or calculated. With coatings, the respective film thickness d must likewise be taken into account. This can be achieved by the determination of Fresnel coefficients and by a transfer matrix approach, which will be described in more detail in the following. The further parameters of the Drude equation (1) are the peak time $\tau$, the high frequency dielectric constant $\varepsilon_\infty$, and the specific electrical resistance $\rho$. They can be taken into account in the determination of the specific electrical resistance or of the specific conductivity. The solution to equation (1) takes place by numerical optimization algorithms; the least squares method and methods derived therefrom are particularly preferred in this respect.

The behavior of the electromagnetic radiation at the boundary layers of a sample can be taken into account while considering the complex refractive indices of the materials/substances involved at the boundary layers, the angle of incidence and the polarization of the electromagnetic radiation and by calculating the Fresnel coefficients.

It should be considered here in this respect whether the intensity measurement values detected using detectors were detected by electromagnetic radiation incident on detectors after a reflection R or after irradiation through a sample, that is transmission T. The layer thickness d, the total intensity of the electromagnetic radiation for the detected measurement positions of the sample can be calculated in dependence on the wavelength and while taking account of the measurement conditions such as the polarization of the radiation and/or of the angle of incidence from the Fresnel coefficients of the individual boundary layers from which the respective sample (e.g. substrate/layer or layer/layer or layer/air) is formed by a transfer matrix approach or by another mathematical transformation. This in particular relates to the total reflection R and/or to the total transmission T.

On an insufficient agreement of the progressions of detected and calculated intensity measurement values, an adaptation of the assumed parameters of the Drude equation (1) and optionally of the layer thickness of the layer described by the Drude function at a substrate or of the substrate per se takes place. The calculation and the comparison with the progression of the detected intensity values are repeated so often until sufficient agreement of the two progressions has been reached. This can be called a fit (regression). The fit can in particular be carried out by the method of least squares and numerical optimization algorithms derived therefrom (e.g. Levenberg-Marquardt algorithm).

At least 30 detectors, preferably at least 100 detectors, should be arranged in a row during the detection of the intensity measurement values.

The irradiation of the surface should take place at at least an angle in the range 0° up to <90° with respect to the normal of the surface of the sample. On an irradiation (transmission) of a sample transparent to the electromagnetic radiation, the angle of preferably at least almost 0° to the sample normal should be observed, that is the radiation should be directed in as perpendicular a manner as possible onto the surface of the sample. The irradiation and detection can also be carried out simultaneously or sequentially at a plurality of angles of incidence of the electromagnetic radiation. As already expressed, angles of incidence can be selected in this context in the range of 0° to a maximum of 89°.

Angles of incidence in the range from 60° to 80° are preferred if reflected radiation is to be detected, independently of whether a constant angle of incidence or different angles of incidence are to be used.

The irradiation and/or the detection can also take place with polarized electromagnetic radiation. In this case, the alignment of the polarization plane can be changed and the electromagnetic radiation can be emitted and/or correspondingly detected at different polarizations.

The detectors and the sample can in particular be moved along at least one axis relative to one another and in so doing preferably at a constant spacing from one another with large-area samples. A sample can thus be moved in an axis with statically fixed detectors and radiation sources. It can be moved by a correspondingly movable table on which a sample is arranged in an x direction and optionally also in a y direction. However, the unwinding of roll to roll is also possible when the sample is of flexibly deformable material, for example in the form of a film.

The elements forming electromagnetic radiation that ensure an advantageous mapping with respect to sample size and lateral resolution and/or the advantageous homogeneous illumination of the sample surface can be present at the radiation source. This element can be a microscope in an embodiment. It can, however, also be a hollow body having an advantageously arranged radiation source (or a plurality thereof) that can direct an electromagnetic radiation diffusely and thus homogeneously onto the surface to be irradiated. The hollow body can be a sphere or a cylinder. A surface to be detected simultaneously should be homogeneously irradiated. With a radiation source with beam-shaping optical elements, the utilized wavelength range should be taken into account in the selection of the respectively used optical elements serving the beam shaping.

A diaphragm that avoids the incidence of scattered electromagnetic radiation can preferably be arranged in front of the detectors in the optical beam path of the electromagnetic radiation.

Electromagnetic radiation whose wavelengths start at UV radiation and end at IR radiation can be emitted by the radiation source. Radiation from the spectral range from 250 nm to 25,000 nm is particularly preferred. Where possible, all the wavelengths within the respective interval should be able to be used for irradiation in a utilized wavelength range. The boundaries should be predefined solely by the sensitivity range of the detectors used and the optical properties of the beam guiding components.

At least one element with which a direct choice of the polarization of the electromagnetic radiation can be achieved can also be present there or can be integrated therein.

A sample can also be a multilayer design of a plurality of layers formed from different materials or substances. It can, for example, be a substrate on which layers at least partially transparent for the electromagnetic radiation used are formed. The substrate can also be correspondingly transparent in this context. The transparency can relate to a portion of the wavelength spectrum of the emitted electromagnetic radiation and/or to a non-absorbed portion of the total wavelength spectrum of the radiation.

The detectors used and the electronic evaluation unit as well as optionally also the radiation source can also represent a so-called hyper-spectral image system that can be used in the arrangement in accordance with the invention.

The spectra detected simultaneously with spatial resolution can be evaluated as follows with respect to the material parameter or substance parameter of interest or of its property (at each detected position).

A combination of different measurement conditions can take place. In this respect, a transmission/reflection measurement, a combination of different angles of incidence, the use and combination of different polarization planes of the electromagnetic radiation can be combined with one another in the most varied forms.

There is also the possibility of using a plurality of row arrangements or of row and column arrangements that can then be arranged after one another in the direction of movement, for example. These arrangements of detectors can each detect under different measurement conditions.

Detection can take place under different measurement conditions using arrangements of detectors whose line/row is configured or can be modified by a use of different optical arrangements (different optical elements).

A substantially higher spatial resolutions up to an almost complete taking into account of the total surface of a sample or coating can be achieved with respect to known measurement processes. A complete or almost complete quality control can be achieved, and indeed also directly in a manufacturing or machining process.

The invention can be used in different technical areas, for example in the semiconductor industry, in photovoltaic manufacture, the manufacture of actively usable panels such as touch screens, flat screens, in the manufacture of antielectrostatic devices, of electrode materials, of panel heating devices or of light sources (OLEDs). The specific electrical resistance of layers composed of an optically transparent oxide (TCO) such as in particular indium tin oxide (ITO) can thus be determined with spatial resolution, for example.

The invention will be explained in more detail by way of example in the following.

There are shown:

FIG. 1 in a schematic form, how the specific electrical resistance can be determined in a manner in accordance with the invention; and FIG. 2 In schematic form, a possible procedure for determining the specific electrical resistance of a layer of ITO on a substrate composed of a glass BK7.

The invention claimed is:

1. An arrangement for the spatially resolved determination of the specific electrical resistance and/or of the specific electrical conductivity of a sample and/or of at least one layer formed on a surface of a sample at different positions, in which
  a plurality of detectors that are configured for a spatially resolved spectral analysis of electromagnetic radiation within a wavelength interval are arranged in a row arrangement or in a row and column arrangement; and
  the detectors are connected to an electronic evaluation unit and are arranged such that electromagnetic radiation emitted by a broadband radiation source impacts the detectors either after reflection at the surface of the sample, at a layer formed on the sample or at the surface of a layer within the sample and/or after the transmission of electromagnetic radiation through a sample transparent for the electromagnetic radiation; wherein
  the irradiation takes place such that a homogeneous intensity of the electromagnetic radiation is observed on a surface from which the electromagnetic radiation is reflected or through which it is transmitted; and
  the electronic evaluation unit is configured such that
  the measurement signals of the detectors detected with spatial resolution and wavelength resolution within a wavelength interval for each detected position are compared with a wavelength-resolved function that by calculation of the propagation of electromagnetic radiation in multilayer systems, in particular while taking account of the Fresnel formulas, using an optical model for a physical description of the examined sample while taking account of the wavelength-dependent progressions of the linear optical refractive indices n and of the absorption coefficients k of all the materials and/or substances forming the sample, wherein that of the material or substance of interest can be approximated by a physical function (description) of the complex refractive index of the conductive material or substance, in particular by the Drude model, and are (iteratively) brought to a sufficient overlap with a calibration curve progression by an advantageous change of the parameters of the physical function, in particular of Drude parameters, to determine the specific electrical resistance and/or the specific electrical conductivity with spatial resolution at different positions.

2. An arrangement in accordance with claim 1, characterized in that the electronic evaluation unit is configured such that an adaptation of the calculated curve progression to the curve progression of a calibration can be achieved iteratively by varying parameters of the Drude equation.

3. An arrangement in accordance with claim 1, characterized in that the irradiation of the surface takes place at least an angle in the range from 0° up to <90° in relation to the normal of the surface of the sample.

4. An arrangement in accordance with claim 1, characterized in that the angle of incidence of the electromagnetic radiation is preferably changeable or settable in the region from 60° to 80°, whereby the detection and evaluation preferably being able to be carried out at a plurality of different angles of incidence.

5. An arrangement in accordance with claim 1, characterized in that the detection and evaluation can be carried out while using a polarizer having a defined, known polarization plane in relation to the plane of incidence.

6. An arrangement in accordance with claim 1, characterized in that the lateral distribution of the layer thickness (es),
  the optical refractive constant(s) or its/their wavelength-dependent progression,
  the absorption constant(s) or its/their wavelength-dependent progression
  of the surface quality or interface quality (roughness) of the sample or of at least one layer formed on the sample,
  the charge carrier concentration and/or the number and/or size and/or shape of defects and/or of particles in the sample or in at least one layer can be determined.

7. An arrangement in accordance with claim 1, characterized in that the detectors and the sample are movable along at least one axis relative to one another and in so doing preferably at a constant spacing from one another.

8. An arrangement in accordance with claim 1, characterized in that the radiation source has optical elements forming the electromagnetic radiation or a radiation source that emits an electromagnetic radiation diffusely over the surface, and that is in particular arranged within a hollow body and a diaphragm that avoids the incidence of scattered electromagnetic radiation is particularly preferably arranged in front of the detectors in the optical path of the electromagnetic radiation.

9. An arrangement in accordance with claim 1, characterized in that the sample is a multilayer design of a plurality of layers formed from different materials or substances.

* * * * *